(12) United States Patent
Malard et al.

(10) Patent No.: US 10,675,594 B2
(45) Date of Patent: Jun. 9, 2020

(54) ACRYLONITRILE-BASED MEMBRANE WITH LOW THROMBOGENICITY

(71) Applicant: GAMBRO LUNDIA AB, Lund (SE)

(72) Inventors: Benjamin Malard, Villette d'Anthon (FR); Corine Lambert, Bully (FR)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 16/329,887

(22) PCT Filed: Aug. 31, 2017

(86) PCT No.: PCT/EP2017/071820
§ 371 (c)(1),
(2) Date: Mar. 1, 2019

(87) PCT Pub. No.: WO2018/050437
PCT Pub. Date: Mar. 22, 2018

(65) Prior Publication Data
US 2019/0224631 A1    Jul. 25, 2019

(30) Foreign Application Priority Data
Sep. 14, 2016  (EP) .................................. 16188681

(51) Int. Cl.

| A61M 1/16 | (2006.01) |
| B01D 67/00 | (2006.01) |
| B01D 69/02 | (2006.01) |
| B01D 71/42 | (2006.01) |
| B01D 69/06 | (2006.01) |
| B01D 69/08 | (2006.01) |
| A61M 1/34 | (2006.01) |

(52) U.S. Cl.
CPC .............. *B01D 71/42* (2013.01); *A61M 1/16* (2013.01); *A61M 1/3413* (2013.01); *B01D 67/0027* (2013.01); *B01D 67/0088* (2013.01); *B01D 67/0093* (2013.01); *B01D 69/02* (2013.01); *B01D 69/06* (2013.01); *B01D 69/08* (2013.01); *B01D 2323/08* (2013.01); *B01D 2323/12* (2013.01); *B01D 2323/38* (2013.01); *B01D 2323/46* (2013.01); *B01D 2325/16* (2013.01); *B01D 2325/18* (2013.01)

(58) Field of Classification Search
None
See application file for complete search history.

(56) References Cited

U.S. PATENT DOCUMENTS

| 6,010,475 A | 1/2000 | Thomas et al. |
| 2011/0305872 A1* | 12/2011 | Li ........................... A61L 29/06 428/141 |
| 2012/0145626 A1 | 6/2012 | Luttropp et al. |

FOREIGN PATENT DOCUMENTS

| EP | 2253369 | 11/2010 |
| WO | WO2007/148147 | 12/2007 |

OTHER PUBLICATIONS

PCT Search Report and Written Opinion prepared for PCT/EP2017/071820, completed Nov. 30, 2017.

* cited by examiner

Primary Examiner — Bradley R Spies
(74) Attorney, Agent, or Firm — Barnes & Thornburg LLP

(57) ABSTRACT

The present disclosure relates to improved semipermeable membranes based on acrylonitrile copolymers for use in dialyzers for the extracorporeal treatment of blood in conjunction with hemodialysis, hemofiltration or hemodiafiltration. The present disclosure further relates to methods of producing such membranes.

22 Claims, 2 Drawing Sheets

A)

B)

ACRYLONITRILE-BASED MEMBRANE WITH LOW THROMBOGENICITY

CROSS-REFERENCE TO RELATED APPLICATIONS

This application is the U.S. national phase of PCT/EP2017/071820, filed on Aug. 31, 2017, which claims the benefit of European Patent Application Serial Number 16188681.7, filed on Sep. 14, 2016, the entire disclosures of both of which are incorporated herein by reference.

TECHNICAL FIELD

The present disclosure relates to improved semipermeable membranes based on acrylonitrile copolymers for use in dialyzers for the extracorporeal treatment of blood in conjunction with hemodialysis, hemofiltration or hemodiafiltration. The present disclosure further relates to methods of producing such membranes.

DESCRIPTION OF THE RELATED ART

Semipermeable membranes for blood treatment based on acrylonitrile copolymers are known. For example, membranes made from the acrylonitrile-sodium methallylsulfonate copolymer, called AN69, are commercially available. A review of the state of the art for AN69 membranes can be found in Thomas et al., Contrib Nephrol. 2011; 173:119-29. An asymmetric semipermeable membrane comprising a support layer and at least one dense, mesoporous or microporous surface layer defining a separating layer has also been described, for example, in U.S. Pat. No. 5,145,583 A, wherein said membrane contains at least one hydrophobic polymer and at least one water-insoluble copolymer. The copolymer comprises acrylonitrile and at least one sulfonic monomer, wherein the concentration of copolymer in the outer surface of said separating layer is higher than the mean copolymer concentration in the membrane as a whole, and wherein said membrane is water-wettable in the dry state. The fibers are obtained by lowering the temperature of a polymer solution extruded from a die until a homogeneous gel structure is obtained, followed by a washing operation and then a stretching operation. The resulting membrane is, for example, described in Cohen-Addad et al. (2003), Biomaterials 24, 173-179.

The subject matter disclosed in European patent application EP 0 925 626 A1 is aimed at reducing contact phase activation of blood or plasma coming into contact with a negatively charged semi-permeable membrane with an exchanger for the treatment of blood or plasma by extracorporeal circulation comprising a semi-permeable membrane based on polyacrylonitrile carrying bound negative charges. The invention concerned a device for the treatment of blood or plasma by extracorporeal circulation, comprising a semi-permeable membrane based on polyacrylonitrile carrying bound negative charges wherein, before or after formation of the membrane, at least one neutral or cationic polymer is incorporated into the membrane, in a suitable quantity so as to regulate the overall ionic capacity and the electrokinetic index of the membrane, in a suitable manner. The polymer may be cationic and selected from polyamines, preferably from polyetyleneimines.

US 2003/0021826 A1 proposed binding, in a stable manner to the surface of semi-permeable membranes essentially constituted by a copolymer of acrylonitrile and at least one anionic and anionizable monomer, an anticoagulation agent which can exert its anticoagulating activity without being leached out into the blood or plasma during treatment by extracorporeal circulation and to reduce the quantity of anticoagulation agent used systemically in the patient during an extracorporeal blood treatment session. The invention concerned a semi-permeable composite membrane comprising a semi-permeable support membrane and an anticoagulation agent suitable for the treatment of blood or plasma by extracorporeal circulation, said semi-permeable support membrane being essentially constituted by a polyacrylonitrile carrying anionic or anionizable groups; the surface of the semipermeable support membrane intended to be brought into contact with the blood or plasma was coated in succession with a cationic polymer carrying cationic groups which can form an ionic bond with anionic or anionizable groups of polyacrylonitrile, the cationic polymer (for example polyethyleneimine, PEI) comprising chains of a size which is sufficient not to traverse the semi-permeable support membrane, and an anticoagulation agent carrying anionis groups which are capable of forming an ionic bond with cationic groups of said cationic polymer (for example heparin).

WO 2007/148147 A1 describes the use, on a membrane preferably based on a copolymer of acrylonitrile and sodium methallylsulfonate, of a solution of a polymer carrying anionic or anionizable groups in the colloidal form and in an acidic medium, in particular by mixing, for example, a solution of polymer carrying anionic or anionizable groups with a solution of organic polyacid in a specific proportion with respect to said polymer, which results in an increase in both the quantity of polymer grafted to the surface of the membrane and the availability of free cationic or cationizable groups at the surface of this membrane coating. The membrane described thus allows a large quantity of compounds carrying anionic or anionizable groups to be bound. It is suggested for treating septic syndrome, in particular by adsorbing endotoxins contained in the biological fluid, for purifying certain molecules contained in the blood or the plasma by extracorporeal circulation and for reducing systemic anticoagulation in a patient during an extracorporeal blood or plasma treatment. A method for preparing the membrane is also described in WO 2007/148147 A1. Methods for preparing acrylonitrile based membranes are also disclosed in U.S. Pat. No. 5,626,760 A. Methods for producing the hydrogel copolymer comprising acrylonitrile and methallylsulfonate are disclosed, for example, in DE 689 13 822 T2.

EP 1 747 059 A1 discloses a composite membrane comprising (a) a support member that has a plurality of pores extending through the support member and (b) a cross-linked copolymer comprising (i) a cationic monomer and an anionic monomer and/or (ii) a zwitterionic monomer, which cross-linked copolymer fills the pores of the support member. As suitable zwitterionic monomers, 4-imidazoleacrylic acid, 4-aminocinnamic acid hydrochloride, 4-(dimethylamino)-cinnamic acid, 1-(3-sulfopropyl)-2-vinylpyridinium hydroxide inner salt, 3-sulfopropyldimethyl-3-methacrylamido-propylammonium inner salt, and 5-amino-1,3-cyclohexadiene-1-carboxylic acid hydrochloride are mentioned. The composite membranes are used in pervaporation processes to dehydrate aqueous mixtures of organic solvents or to remove water from immiscible or partially miscible mixtures by pervaporation.

JP 2003/320229 A discloses hollow fiber membranes made mainly of polysulfone comprising, in the inner surface, a copolymer of a vinyl polymerizable monomer having a zwitterion in the molecule and another vinyl polymerizable monomer. Phosphobetaines, sulfobetaines and carboxybetaines are mentioned, sulfobetaines being preferred. In the list of polymers suitable for the membrane, polysulfone, PES, PAES, and polyarylate polyethersulfone are mentioned. A polybetaine having a molecular weight ≤5,000 Da is dissolved in the bore liquid at a concentration of 0.001 to 10 wt.-%, preferably 0.01 to 5 wt.-%. According to the reference, the membrane shows low protein absorption and good biocompatibility.

WO 2007/24393 A discloses super-low fouling surfaces coated with polysulfobetaines prepared from one or more monomers selected from the group consisting of sulfobetaine acrylates, sulfobetaine acrylamides, sulfobetaine vinyl compounds, sulfobetaine epoxides, and mixtures thereof and polycarboxybetaines prepared from one or more monomers selected from the group consisting of carboxybetaine acrylates, carboxybetaine acrylamides, carboxybetaine vinyl compounds, carboxybetaine epoxides, and mixtures thereof, respectively. The surfaces are said to be highly resistant to protein adsorption or cell adhesion.

US 2007/056900 A1 teaches to coat the surface of membranes, e.g., hollow fiber membranes, based on polysulfones, PES, PAES, polyarylsulfone, polyamide and others, and blended with hydrophilic polymers like PVP, with copolymers of, among other N-vinylamines or N-vinyllactams, N-vinylpyrrolidone or N-vinylimidazole with (meth)acrylic acid derivatives. Example 16 discloses a copolymer of vinylpyrrolidone and methacrylamidopropyl dimethylammoniopropyl sulfobetaine (SPP).

SUMMARY

It is an object of the present invention to provide a membrane which is based on a copolymer of acrylonitrile and sodium methallylsulfonate for use as a membrane in the extracorporeal treatment of blood, wherein the membrane shows reduced thrombogenicity. The membrane is coated with a mixture of at least one cationic polymer and a zwitterionic compound. It is also an object of the present invention to provide for hollow fiber membranes useful for producing a device for the extracorporeal purification of blood.

BRIEF DESCRIPTION OF THE DRAWINGS

FIG. 2A shows TAT formation over time, while FIG. 2B depicts the build-up of blood pressure in the capillaries.

DETAILED DESCRIPTION

Figure 1:
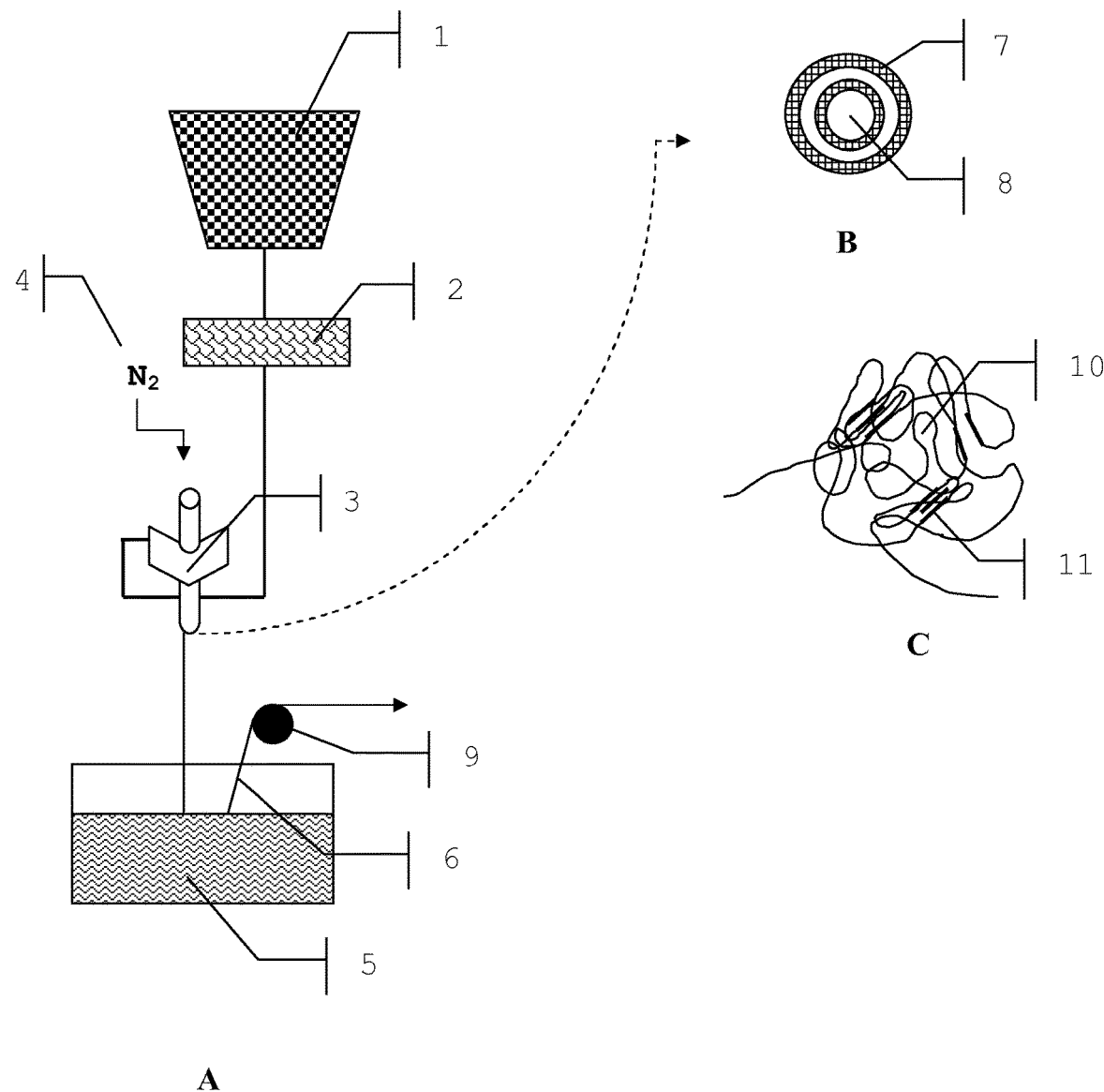
FIG. 1A is a schematic representation of the phase inversion spinning process which is used for preparing membranes according to the invention. The container (1) contains the starting components, such as, for example, DMF, glycerol and acrylonitrile-sodium methallylsulfonate (AN69) copolymer in the form of impregnated granules. The mixture passes a heating extrusion screw (2) and after that enters the spinning head (3).
FIG. 1B depicts a schematic close-up cross-section view of the spinning nozzle (3). Two concentric rings (7) enclose the polymer solution. Nitrogen (4) forms the center medium or core fluid which is blown into the center (8) of the spinning nozzle. A "preformed" hollow fiber leaves the nozzle and enters the spinning bath (5) which comprises water at an elevated temperature. The fiber (6) is taken up by rollers (9) at a speed which is slightly higher than the speed with which the fiber leaves the nozzle. The fiber is thus stretched in the hot water bath, leading to a partial transformation of amorphous zones (10) in the membrane to so-called "pseudo crystalline" zones (11). This transformation is schematically depicted in FIG. 1C. The final stretching in the hot water bath is an essential step of the method as disclosed in this application and determines, among other parameters, the final hollow fiber dimension and performance.

Membranes based on acrylonitrile copolymers have long since been known in the art and are commercially available still today, for example the membranes often collectively referred to as "AN69" membranes. In the context of the present invention, the term "AN69 membrane" or "AN69 type membrane" refers to membranes based on a copolymer of sodium methallylsulfonate and acrylonitrile. The AN69 membranes are known for their high water content of up to 69%, for some types even up to 74%. In the present disclosure, the values recited for water content of membranes refer to the equilibrium water content of the respective membrane under ATPS conditions, i.e., at ambient temperature and ambient pressure, and in air saturated with water vapor.

One example for a current product comprising a AN69 type membrane is the Evodial® dialyzer, which is a hemodialyzer equipped with a heparin-grafted acrylonitrile-based membrane such as described in the aforementioned WO 2007/148147 A1 (the so-called HeprAN membrane). The Evodial® membrane is characterized also in that the charged surface, originating from anionic sulfonate groups, is neutralized by the polycationic biopolymer polyethylenimine (Thomas et al. (2011), Contrib Nephrol. Basel, Karger, vol 173, 119-129). The surface treatment also allows the almost irreversible fixing of said heparin through very strong ionic binding between the negative charges of heparin and the free positive charges of the cationic polymer. Membranes having the ability to immobilize heparin are highly desirable as it further reduces the need of systemic doses of heparin, and might even allow heparin-free dialysis possible especially for patients with high risk of bleeding (Thomas et al., Contrib Nephrol. 2011; 173:119-29).

AN69 membranes are formed based on a copolymer prepared from sodium methallylsulfonate and acrylonitrile. It is possible to use other co-monomers instead of sodium methallylsulfonate. However, sodium methallylsulfonate is used as a specific, well known example for any such co-monomer throughout the present disclosure without wanting to limit the invention to said methallylsulfonate only. The molar ratio of acrylonitrile and the sodium methallylsulfonate in the AN69 copolymer lies in the range of from 90:10 and 99:1. According to one embodiment of the invention, the molar ratio lies in the range of from 90:10 and 95:5. The AN69 membrane is hydrophilic because the numerous sulfonate groups attract water and create a hydrogel structure which provides high diffusive and hydraulic permeability. In the AN69 membrane the microstructure and the chemical composition offer a context for bulk adsorption of small proteins. The relatively high water content of the hydrogel generally makes the polymer chains easily accessible. The said water content and the related structure of acrylonitrile based hydrogel membranes of the prior art, specifically those based on sodium methallylsulfonate and acrylonitrile, is strongly influenced by the way the membranes are produced.

The AN69 membranes are generally produced by a phase inversion process making use of a hydrogel which is derived from a copolymer of acrylonitrile and sodium methallylsulfonate. The manufacturing process for AN69 hollow fiber membranes is based on high temperature spinning and the use of nitrogen as center medium when hollow fibers are produced (FIG. 1). Hollow fibers are obtained by preparing a composition of a copolymer of acrylonitrile and sodium methallylsulfonate, N,N-dimethyl formamide (DMF), and glycerol and heating it to a temperature of from 110° C. to 150° C. before the composition enters the spinning nozzle, for example by means of a heating extrusion screw. According to one embodiment of the invention, the temperature is in the range of from 130° C. to 145° C. For the membranes used in the Examples, a temperature of 140° C. was chosen. The amount of the copolymer is generally adjusted to 34 to 36 wt.-%. For the membranes used in the Examples, the amount of copolymer was chosen to be 35 wt.-%. DMF or any other solvent which can be used, such as, for example, dimethylsulfoxide (DMSO) or N-methylpyrrolidone (NMP), is present in the composition in an amount of from about 50 to 58 wt.-%; and glycerol is present in an amount of from 6 to 16 weight-%. Of course, all components of the composition will add up to a total of 100%. According to one embodiment of the present invention, the copolymer is present in the composition in an amount of 35 wt.-%, DMF is present in the composition in an amount of 52 wt.-%, and glycerol is present in an amount of 13 wt.-%. The composition is then passed through a spinneret. The extrusion is carried out in the presence of the aforementioned inert nitrogen as center medium. The fiber then enters a spinning bath (see FIG. 1A).

The spinning bath is set up in a certain distance to where the fiber leaves the spinneret. The distance usually is in the range of from 0.8 to 1.9 m. The gap between nozzle and spinning bath contains ambient air at ambient temperature. Usually, the gap is located in a sealed cabin to prevent vapors from spreading. In the prior art, the spinning bath is adjusted to temperatures of from −4° C. to 20° C. Typical spinning bath temperatures for known AN69 membranes are in the range of from 6° C. to 20° C. For example, a standard spinning bath temperature for AN69 membranes is 10±2° C. The initial spinning bath usually consists of water. Optionally, additives such as $H_2O_2$ can be added in order to prevent bacterial growth. However, it is possible to add an organic solvent to the spinning bath. The solvents can be chosen from the same solvents which are used for forming the initial polymer composition.

Following the submersion into the spinning bath, the fiber can subsequently be subjected to an operation of stretching at a temperature of about 90° C. to 100° C., generally at about 95° C. The stretching operation is done while the fiber is still immersed in water, and the desired temperature can be achieved by heating the water accordingly. The stretching can be achieved by adjusting the speed of the uptake rollers (FIG. 1A) onto which the fibers are transferred from the spinning bath. It is known that the stretching ratio is impacting the formation and ratio of certain amorphous membrane zones and pseudo-crystalline zones of certain membrane types (Xi et al.: *Polymers for advanced Technologies* 19 (2008) 1616-1622). Stretching ads to the alignment of amorphous zones which in turn increases the structural integrity of the resulting membrane (FIG. 1C). An increased stretching ratio may further increase the Lp of the membrane to a certain extent. The expression "Lp" or "hydraulic permeability" as used herein refers to the permeability of the membrane to water or an aqueous solution (saline solution), hereinafter referred to as "liquid". Hydraulic permeability expresses how readily the liquid can move across a membrane and has units of volume of liquid per unit area of membrane per unit time per unit driving force.

The stretching ratio is defined by the take-up speed of the second roller which is higher compared to the take-up speed of the first roller. According to the present invention, the ratio preferably is in a range of from 3.6 to 4.5. According to a specific embodiment of the invention the stretching ratio is in a range of from 3.6 to 4.1. Stretching ratios of 5 or higher are undesirable because they may result in damaged or torn fibers. High stretching ratios may also result in a phenomenon referred to as "crystallization under constraint", which refers to an extended reorganization of the amorphous zone, leading to a behavior which is typical rather for impermeable crystalline zones.

It was found that a membrane having low thrombogenicity can be obtained by treating a membrane based on a copolymer prepared from sodium methallylsulfonate and acrylonitrile with a polycationic polymer and a zwitterionic compound. Membranes according to the invention which are characterized by a polycationic polymer and a zwitterionic compound grafted to their surface are a further object of the present invention.

According to the invention, the membranes are treated by ionic grafting of a polycationic polymer selected from the group consisting of polyamines, such as cationic polyaminoacids and/or polyimines, comprising polylysine, polyarginine, polyethyleneimine (PEI) and copolymers and mixtures thereof. According to a specific embodiment of the present invention, said polycationic polymer is PEI. Such grafting can be done by methods known in the art and as described, for example, in U.S. Pat. No. 6,423,232 B1 and WO 2007/148147 A1.

According to the invention, the membranes are also treated by ionic grafting with a zwitterionic compound. Examples of suitable zwitterionic compounds include phosphobetaines, sulfobetaines, and carboxybetaines. Suitable phosphobetaines include compounds derived from phosphobetaine methacrylate (PBMA). Suitable sulfobetaines include compounds derived from sulfobetaine methacrylate (SBMA). Suitable carboxybetaines include compounds derived from carboxybetaine methacrylate (CBMA).

In one embodiment of the invention, sulfobetaines are used. In one embodiment, the sulfobetaine is (2-(methacryloyl-oxy)ethyl)dimethyl (3-sulfopropyl)ammonium hydroxide (SBMA). In one embodiment, monomeric SBMA is used. In another embodiment, oligomeric SBMA is used. In still another embodiment, polymeric SBMA (polySBMA) having a weight-average molecular weight in the range of from 50 kDa to 300 kDa, for instance, 120 kDa to 150 kDa, is used. Such polymers can be produced by free-radical polymerization, as described in Langmuir 2010, 26 (22), 17286-17294.

In one embodiment of the invention, the sulfobetaine is poly(3-((2-methacryloyloxyethyl)dimethylammonio)propyl-1-sulfonate-co-vinylpyrrolidone), a copolymer of vinylpyrrolidone and 3-((2-methacryloyloxyethyl)dimethylammonio)propyl-1-sulfonate, also known as SPE, which is commercially available from Raschig GmbH, D-67061 Ludwigshafen, under the trade name Ralu®Mer SPE. In another embodiment of the invention, the additive is a copolymer of vinylpyrrolidone and 3-((2-acryloyloxyethyl)dimethylammonio)propyl-1-sulfonate, also known as SPDA, which is commercially available from Raschig GmbH, D-67061 Ludwigshafen, under the trade name Ralu®Mer SPDA.

In one embodiment of the invention, ionic grafting is performed by treatment of the membrane with an aqueous solution of the polycationic polymer and an aqueous solution of the zwitterionic compound. In one embodiment, the membrane is first treated with the aqueous solution of the polycationic polymer and subsequently with the aqueous solution of the zwitterionic compound. In another embodiment, the sequence of treatment is reversed. In still another embodiment, the membrane is simultaneously treated with both the polycationic polymer and the zwitterionic compound.

Ionic grafting of membranes with polycationic polymers has been described in WO 2007/148147 A1. One embodiment uses polyethyleneimine (PEI) in an acidic medium. Under these conditions, PEI takes a linear conformation. This conformation of PEI maximizes accessibility of positively charged amino groups at the membrane interface (see K. Gibney et al., "Poly(ethylene imine)s as antimicrobial agents with selective activity", *Macromol. Biosci.* 12 (9) (2012) 1279-1289). On the other hand, an excess of amino groups at the membrane interface may trigger the coagulation cascade, potentially via platelet activation. An adequate ratio between PEI and the zwitterionic compound is required to obtain the desired effect. In one embodiment of the invention using SBMA as the zwitterionic compound, the weight ratio (w/w) of PEI and SBMA is in the range of from 1:5 to 1:20, e.g., 1:10.

It is known that the AN69 type membranes have a remarkable ability to immobilize certain uremic toxins, including larger middle molecules, to their surface by adsorption. The membranes of the present invention can efficiently be used to remove uremic toxins from a patients suffering from kidney damage. Due to their specific characteristics, they are capable of removing an extended range of molecules in terms of the molecular weight of the toxins, encompassing molecules which are generally referred to as middle molecules. The term "middle molecules", as it is used in the context of the present invention, refers to molecules having a molecular weight between 15 kDa and 60 kDa, specifically to molecules having a molecular weight between 15 kDa and 45 kDa, even though in the prior art this expression is sometimes used for a broader range of molecules.

The membranes of the present invention which comprise both a polycationic polymer and a zwitterionic moiety show lower thrombogenicity than membranes modified only with a polycationic polymer like PEI. They also show lower thrombogenicity than membranes modified with a polycationic polymer and heparin ("HeprAN membrane").

The membrane of the present invention may be a flat sheet membrane or a hollow fiber membrane. According to one aspect of the present invention, the membrane is a hollow fiber membrane which is composed of a homogeneous and symmetrical polyelectrolytic hydrogel derived from a copolymer of acrylonitrile and methallylsulfonate. Flat sheet membranes can also be prepared according to methods known in the art.

The hollow fibers according to the invention have an internal diameter of from approximately 180 to approximately 260 µm. According to one embodiment of the invention, inner diameter will be in the range of from 50 to 250 µm. The wall thickness will generally be in the range of from 35 to 60 µm, preferably in a range of from 40 to 50 µm.

As mentioned above, it is a further object of the present invention to provide a hollow fiber membrane useful for producing a device for the extracorporeal purification of blood. According to one aspect of the present invention, the hollow fiber is composed of a homogeneous and symmetrical polyelectrolytic hydrogel as described above. According to another aspect of the invention, the hollow fibers used each have an internal diameter of from 50 to 260 µm, in most cases of from 180 to 250 µm. The surface area of a dialyzer comprising hollow fiber membranes according to the invention may vary, but will usually be in a range of from 1.0 to 2.3 $m^2$. Dialyzers comprising the membrane of the invention can be assembled as known in the art. Sterilization of the devices will normally be done by irradiation with gamma rays or using ETO.

The membranes of the invention and dialyzers comprising said membranes, apart from being useful in hemodialysis or hemodiafiltration treatment as mentioned before, may be used for the treatment of chronic kidney disease patients who will benefit from the extended range of molecules which can be removed by the membrane. Due to the aforementioned adsorption capacities which allow the removal of an extended range of molecules, comprising molecules of up to about 60 kDa, combined with significantly improved convective properties, the membranes and hemodialyzers of the invention can be especially beneficially used in CRRT. Continuous renal replacement therapy (CRRT) is any extracorporeal blood purification therapy designed to substitute for impaired renal function over an extended period, and intended to be applied for up to 24 hours a day. CRRT is a modality specifically designed for treating ICU patients with acute kidney injury (AKI), especially in the case of hemodynamically unstable AKI patients. The membranes and dialyzers of the invention can also be used in cascade filtration systems.

Devices according to the invention can be used on known dialysis machines with blood flow rates of between 150 ml/min and 500 ml/min. Average blood flow rates will be in the range of between 200 and 500 ml/min. The devices comprising membranes according to the invention can be used in hemodialysis as well as in hemodiafiltration (HDF) mode, including pre- and post-dilution.

The expression "HDF" as used herein refers to hemodiafiltration. While hemodialysis (HD) is primarily based on diffusion, thus relying on differences in concentration as the driving force for removing unwanted substances from blood, hemodiafiltration (HDF) also makes use of convective forces in addition to the diffusive driving force used in HD. Said convection is accomplished by creating a positive pressure gradient across the dialyzer membrane. Accordingly, blood is pumped through the blood compartment of the dialyzer at a high rate of ultrafiltration, so there is a high rate of movement of plasma water from blood to dialysate which must be replaced by substitution fluid that is infused directly into the blood line. Dialysis solution is also run through the dialysate compartment of the dialyzer. Hemodiafiltration is used because it may result in good removal of both large and small molecular weight solutes. The substitution fluid may be prepared on-line from dialysis solution wherein the dialysis solution is purified by passage through a set of membranes before infusing it directly into the blood line.

It will be readily apparent to one skilled in the art that various substitutions and modifications may be made to the invention disclosed herein without departing from the scope and spirit of the invention.

EXAMPLES

Example 1

Preparation of AN69 Hollow Fibers

Hollow fibers as shown herein were obtained using a gelification process that consists of processing a collodion composed of acrylonitrile and sodium methallylsulfonate (91:9) (35 wt.-%), DMF (52 wt.-%) and glycerol (13 wt.-%), and as further described in FIG. 1. The spinning nozzle temperature was adjusted to 140° C. The center medium was nitrogen (inert gas). The default spinning bath temperature was set to 10° C. The distance of the spinneret to the spinning bath was set to 1 m. Stretching was performed at about 95° C.

Example 2

Preparation of Hollow Fiber Modules

Mini-modules comprising samples of 280 fibers of the hollow fiber membranes obtained in Example 1 were prepared. The mini-modules had a length of 24 cm. The 280 fibers were isolated from each other by using polyurethane glue at one ending. The fibers were re-opened at the potted end by cutting the bundle at its extremity. The effective membrane surface area (A) of the fibers amounted to 500 cm². The non-potted extremity was clamped during the experiment.

a) Control 20 mg/kg PEI

The mini-modules were first rinsed with water for 5 min to remove residual glycerol. Subsequently, they were perfused with an aqueous solution comprising 20 mg/kg polyethyleneimine (PEI) in citric acid (ratio PEI/Ac=1) at pH 4 for 5 min at a flow rate of 6 ml/min. Finally, they were rinsed with water again. The procedure is similar to the one described in WO 2007/148147 A1.

b) HeprAN Type

The mini-modules were first rinsed with water for 5 min to remove residual glycerol. Subsequently, they were perfused with an aqueous solution comprising 200 mg/kg polyethyleneimine (PEI) in citric acid (ratio PEI/Ac=1) at pH 4 for 5 min at a flow rate of 6 ml/min. They were rinsed with water for 90 sec; and then they were perfused with an aqueous solution of 100 UI/ml heparin at a flow rate of 3 ml/min for 4 min 30 sec. Finally, they were rinsed with water again.

c) 20 mg/kg PEI+200 mg/l SBMA

The mini-modules were first rinsed with water for 5 min to remove residual glycerol. Subsequently, they were perfused with an aqueous solution comprising 20 mg/kg polyethyleneimine (PEI) in citric acid (ratio PEI/Ac=1) at pH 4 for 5 min. They were rinsed with water for 90 sec; and then they were perfused with an aqueous solution of 200 mg/l SBMA at a flow rate of 3 ml/min for 10 min. Finally, they were rinsed with water again.

Example 3

Determination of Thrombogenicity

The mini-modules were first rinsed with 30 ml of 0.9% sodium chloride solution at a flow rate of 3 ml/min; and any residual air was removed from the mini-modules. A sample of 30 ml of blood comprising 4 mmol/l $Ca^{2+}$ was circulated through each mini-module in a closed loop at a temperature of 37° C. and at a flow rate of 12 ml/min.

Coagulation Test: Blood Pressure and TAT Measurement a) Monitoring of TAT Formation

TAT (thrombin/antithrombin III complex) formation was monitored by sampling 1.5 ml blood from the circuit at the times indicated below and adding 0.2 ml of citric acid (CTAD) to the sample. This procedure stops the coagulation process in the sample. All samples were then cryopreserved at −30° C. until further analysis using a TAT assay. TAT was measured with an enzyme-linked immunosorbent assay from a commercial kit (Enzygnost® TAT micro, Siemens, Newark, USA). The results are summarized in the following table:

| | TAT (µg/L) | | |
|---|---|---|---|
| | Control PEI (20 mg/kg) | HeprAN type | PEI (20 mg/kg) + SBMA (200 mg/l) |
| 0 | 25 | 28.52 | 25.96 |
| 10 | 132.98 | | |
| 11 | | | 55.72 |
| 45 | 436.33 | | |
| 97 | | 206.26 | 78.93 |
| 114 | | 457.65 | |
| 180 | | | 142.24 | b) Monitoring of Blood Pressure

Close surveillance of the inlet pressure of the mini-module was performed to evaluate coagulation in the system. In the experimental set up (closed loop model using a blood container), the outlet pressure is considered negligible (no effect of the venous access like in an in vivo configuration). An increase of inlet pressure over time is reflecting coagulation in the module. In the experimental set up, an increase in blood viscosity can only be attributed to a coagulation phenomenon, considering that there is no fluid exchange in the system (neither dilution nor hemoconcentration). The absolute inlet pressure is specific for each module at the start of the experiment. The inlet pressure was therefore normalized by using the delta pressure (P blood inlet (t)−P blood inlet (t0)) to allow comparative graphical representation. The results of the measurements are summarized in the following table:

| | Blood P(t)-P(t0) (mmHg) | | |
|---|---|---|---|
| | Control PEI (20 mg/kg) | HeprAN type | PEI (20 mg/kg) + SBMA (200 mg/l) |
| 0 | 0 | 0 | 0 |
| 11 | | 14 | 28 |
| 13 | 0 | | |
| 24 | 1 | | |
| 30 | | 22 | 33 |
| 43 | 20 | 28 | 30 |
| 50 | 400 | 29 | 28 |
| 97 | | 42 | 38 |
| 113 | | 91 | 38 |
| 118 | | 434 | |
| 132 | | | 42 |
| 180 | | | 53 |

Figure 2:
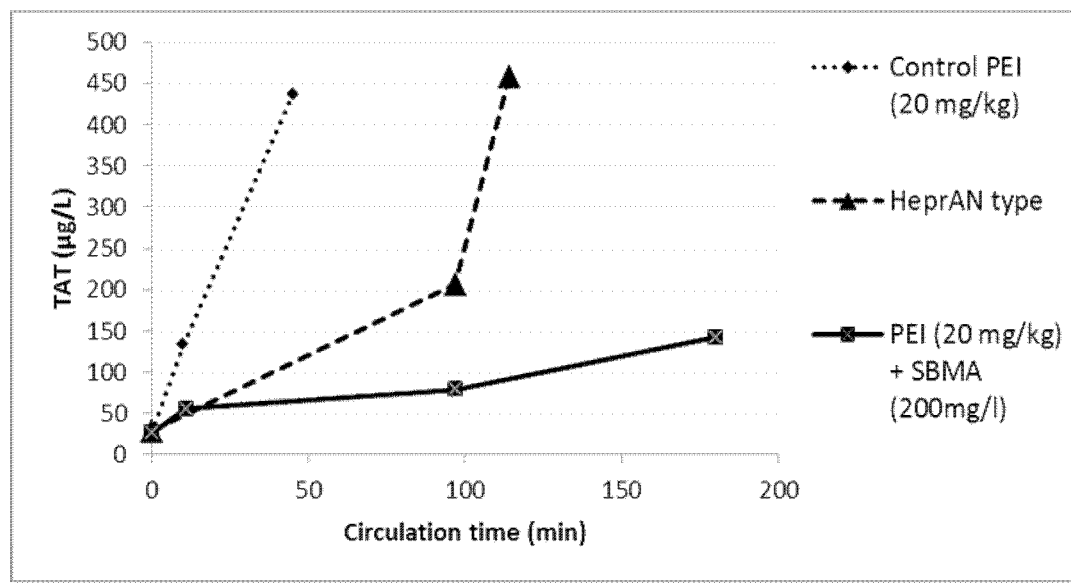
FIG. 2 illustrates the results of an evaluation of the thrombogenicity of different hollow fiber membranes, as described in Example 3.
Figure 2:
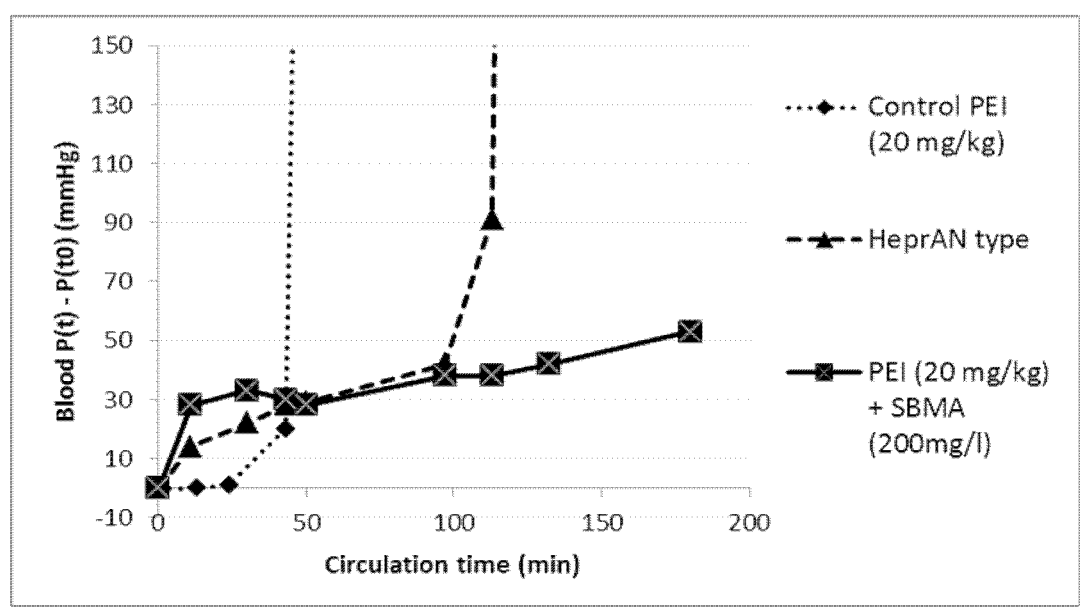

The results of the coagulation tests are depicted in FIG. 2.

The invention claimed is:

1. A membrane comprising a copolymer of acrylonitrile and sodium methallylsulfonate, a polycationic polymer, and a zwitterionic compound,
   wherein the polycationic polymer is polyethyleneimine (PEI),
   wherein the zwitterionic compound is a sulfobetaine, and
   wherein the PEI and the sulfobetaine are ionically grafted on the membrane at a weight ratio in the range of from 1:5 to 1:20 (PEI:sulfobetaine).

2. The membrane of claim 1, wherein the sulfobetaine is derived from (2-(methacryloyloxy)ethyl) dimethyl (3-sulfo-propyl) ammonium hydroxide (SBMA).

3. The membrane of claim 2, wherein the sulfobetaine is monomeric SBMA.

4. The membrane of claim 2, wherein the sulfobetaine is polymeric SBMA having a weight average molecular weight in the range of from 50 to 300 kDa.

5. The membrane of claim 1, wherein the membrane is a flat sheet membrane.

6. The membrane of claim 1, wherein the membrane is a hollow fiber membrane.

7. A method for preparing a hollow fiber membrane according to claim 6, said method comprising the steps of
   (a) forming a polymer composition comprising about 34 to about 36 wt.-% of a copolymer of acrylonitrile and sodium methallylsulfonate in a molar ratio of between about 90:10 and about 99:1, about 50 to about 58 wt.-% of a solvent selected from the group of solvents consisting of DMF, DMSO and NMP, and about 6 to about 16 wt.-% of glycerol, wherein all components add up to 100% in the final polymer composition;
   (b) heating the composition of (a) to a temperature of between about 110° C. and about 150° C.;
   (c) passing the composition through a spinning nozzle comprising two concentric rings which enclose the polymer composition, and a center opening which is perfused with an inert gas;
   (d) after passage of an air gap of between about 0.8 and about 1.9 m passing the preformed hollow fiber of (c) into a spinning bath having a temperature in the range of from about −4° C. to about 20° C.;
   (e) optionally, stretching the hollow fiber membrane in a water bath at a temperature of from about 90° C. to about 100° C. by a factor of from about 2 to about 5;
   (f) treating the hollow fiber membrane with an aqueous solution of a polycationic polymer, wherein the polycationic polymer is polyethyleneimine (PEI); and
   (g) treating the hollow fiber membrane with an aqueous solution of a zwitterionic compound, wherein the zwitterionic compound is a sulfobetaine,
   wherein the PEI and the sulfobetaine are ionically grafted on the membrane at a weight ratio in the range of from 1:5 to 1:20 (PEI:sulfobetaine).

8. The method of claim 7, wherein the sulfobetaine is derived from (2-(methacryloyloxy)ethyl) dimethyl (3-sulfo-propyl) ammonium hydroxide (SBMA).

9. A filter device comprising a membrane wherein the membrane comprises a copolymer of acrylonitrile and sodium methallylsulfonate, a polycationic polymer wherein the polycationic polymer is polyethyleneimine (PEI), and a zwitterionic compound, wherein the zwitterionic compound is a sulfobetaine,
   wherein the PEI and the sulfobetaine are ionically grafted on the membrane at a weight ratio in the range of from 1:5 to 1:20 (PEI:sulfobetaine).

10. The filter device of claim 9, wherein the membrane is a flat sheet membrane.

11. The filter device of claim 9, wherein the membrane is a hollow fiber membrane.

12. The filter device of claim 9, wherein the sulfobetaine is derived from (2-(methacryloyloxy)ethyl) dimethyl (3-sulfo-propyl) ammonium hydroxide (SBMA).

13. The filter device of claim 9, wherein the sulfobetaine is monomeric SBMA.

14. The method of claim 7, wherein the sulfobetaine is monomeric SBMA.

15. The method of claim 7, wherein the sulfobetaine is polymeric SBMA having a weight average molecular weight in the range of from 50 to 300 kDa.

16. The filter device of claim 9, wherein sulfobetaine is polymeric SBMA having a weight average molecular weight in the range of from 50 to 300 kDa.

17. The membrane of claim 2, wherein the sulfobetaine is polymeric SBMA having a weight average molecular weight in the range of from 120 to 150 kDa.

18. The method of claim 7, wherein the sulfobetaine is polymeric SBMA having a weight average molecular weight in the range of from 120 to 150 kDa.

19. The filter device of claim 9, wherein sulfobetaine is polymeric SBMA having a weight average molecular weight in the range of from 120 to 150 kDa.

20. The membrane of claim 2, wherein the PEI and the sulfobetaine are ionically grafted on the membrane at a weight ratio of 1:10 (PEI:sulfobetaine).

21. The method of claim 7, wherein the PEI and the sulfobetaine are ionically grafted on the membrane at a weight ratio of 1:10 (PEI:sulfobetaine).

22. The filter device of claim 9, wherein the PEI and the sulfobetaine are ionically grafted on the membrane at a weight ratio of 1:10 (PEI:sulfobetaine).

* * * * *